United States Patent [19]

Hirose et al.

[11] 4,055,640
[45] * Oct. 25, 1977

[54] COMPOSITIONS AND METHODS FOR CONTROLLING THE GROWTH OF BACTERIA, FUNGI AND ALGAE USING CERTAIN DERIVATIVES OF N-(2,2-DICHLOROVINYL)SALICYLAMIDES

[75] Inventors: Kiyonobu Hirose, Ageo; Shuichi Ishida, Omiya; Kaoru Omori, Okegawa, all of Japan

[73] Assignee: Nippon Kayaku Co., Ltd., Tokyo, Japan

[*] Notice: The portion of the term of this patent subsequent to Oct. 25, 1994, has been disclaimed.

[21] Appl. No.: 649,555

[22] Filed: Jan. 15, 1976

Related U.S. Application Data

[63] Continuation-in-part of Ser. No. 595,748, July 14, 1975, and Ser. No. 595,749, July 14, 1975, abandoned.

[30] Foreign Application Priority Data

Aug. 13, 1975 Japan ................................ 50-97518
July 18, 1975 Japan ................................ 50-88088

[51] Int. Cl.$^2$ ......................... A01N 9/24; A61L 31/60
[52] U.S. Cl. ...................................... 424/230; 210/64
[58] Field of Search ................. 424/230; 260/479 R, 260/480, 559 S

[56] References Cited

U.S. PATENT DOCUMENTS 2,923,737   2/1960   Ruschig et al. ................. 260/559 S

OTHER PUBLICATIONS

Chemical Abstracts, 78:42611r (1973).

Chemical Abstracts, 75:139927z (1971).

*Primary Examiner*—Leonard Schenkman
*Attorney, Agent, or Firm*—Russell & Nields

[57] ABSTRACT

The compounds used in the present invention are represented by the following formula:

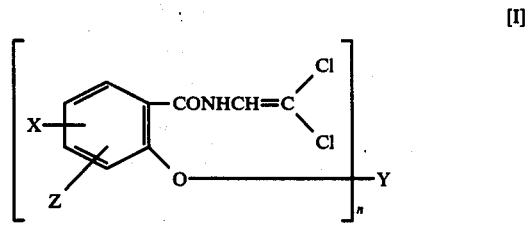

[I]

where X represents hydrogen atom, chlorine atom, bromine atom, methyl group or nitro group, Y represents hydrogen atom, methyl group, an alkylcarbonyl group where the alkyl group has from 1 to 12 carbon atoms, preferably, from 1 to 3 carbon atoms and may be substituted by one or more halogen atoms, a lower alkoxy carbonyl group, a lower alkylamino carbonyl group or a metal atom of which the valence is 1 or 2, Z represents hydrogen atom or chlorine atom and $n$ represents 2 when Y represents a divalent metal and $n$ represents 1 when Y does not represent a divalent metal.

Such compounds are employed to control the growth of bacteria, fungi and algae which propagate on industrial raw materials and products or in water in circulating water systems, and to exterminate bacteria and fungi which harm agricultural and horticultural plants or crops.

8 Claims, No Drawings

COMPOSITIONS AND METHODS FOR CONTROLLING THE GROWTH OF BACTERIA, FUNGI AND ALGAE USING CERTAIN DERIVATIVES OF N-(2,2-DICHLOROVINYL)SALICYLAMIDES

This application is a continuation-in-part of copending U.S. patent application Ser. No. 595,748 filed July 14, 1975 and of U.S. patent application Ser. No. 595,749 filed July 14, 1975 now abandoned.

BACKGROUND OF THE INVENTION

The present invention relates to methods for controlling the growth of bacteria, fungi and algae. The methods of the invention may be used, for example, for controlling bacteria, fungi and algae which propagate on industrial raw materials and products and in water in circulating water systems.

The bacteria and fungi on industrial raw materials and products degrade the quality of industrial raw materials and products and cause various other troubles. The damage is very serious. The algae which propagate on the bottom of ships cause the slowdown of speed of ships. Bacteria, fungi and algae in water in circulating water systems produce mats of slime which restrict the flow of water and reduce the efficiency of heat exchange. The troubles caused by bacteria, fungi and algae constitute a considerable problem.

Many compounds having bactericidal, fungicidal and algicidal activity have been used for prevention of the damage caused by the bacteria, fungi or algae to industrial raw materials and products and the impediment caused by slime in circulating water systems. These compounds include, for example, organic mercury compounds, organic tin compounds, phenols having substituted halogen atoms, organic sulfur compounds, formalin, cresol and quaternary ammonium salts. These compounds, however, have various defects, for example, strong toxicity against humans and live-stock, pollution of environment, irritative or offensive odor, bad influence upon industrial raw materials and products and weak bactericidal and fungicidal activity.

The compounds of the invention also have remarkable exterminating activity against various kinds of bacteria or fungi which harm agricultural and horticultural plants or crops, and such compounds can be used for a foliar treatment, seed treatment and soil treatment. The compounds of the invention are particularly useful for the prevention of soil-borne plant diseases which are caused by fungi and bacteria living in soil.

An excellent agricultural chemical for the prevention of soil-borne plant disease has not been discovered since the use of organic mercury compounds as agricultural chemicals was prohibited on account of the toxic character of the compounds against men and beasts.

SUMMARY OF THE INVENTION

It is, therefore, the object of the present invention to provide new compounds having bactericidal, fungicidal and algicidal activity against bacteria, fungi and algae which propagate on industrial raw materials and products and in water in circulating water systems, to provide methods for controlling such bacteria, fungi and algae and to provide compositions used for the methods.

In addition, the invention includes methods of exterminating bacteria or fungi which harm agricultural and horticultural plants or crops. In particular, when the present compounds are used for soil treatment or seed treatment in the way of dressing seed with a dust, the present compounds exhibit an excellent effect on the prevention of soil-borne plant diseases, for example, damping off of cucumber, Fusarium wilt of cucumber and seedling blight of rice and do not harm agricultural and horticultural plants and crops.

DETAILED DESCRIPTION OF THE INVENTION

Representative compounds useful in the present invention are shown in Table 1

TABLE 1

| Compound No. | Compound | M.P. or $n_D^\xi$ | Appearance |
|---|---|---|---|
| 1 | CONHCH=CCl$_2$, OH (phenyl) | m.p. 160–4° C | White crystals |
| 2 | CONHCH=CCl$_2$, OH, Cl (phenyl) | m.p. 208–10° C | White crystals |
| 3 | CONHCH=CCl$_2$, OH, Br (phenyl) | m.p. 202–4° C | White crystals |
| 4 | CONHCH=CCl$_2$, OH, CH$_3$ (phenyl) | m.p. 78–82° C | White crystals |
| 5 | CONHCH=CCl$_2$, OH, CH$_3$ (phenyl) | m.p. 189–191° C | White crystals |
| 6 | CONHCH=CCl$_2$, OC(O)CH$_3$ (phenyl) | m.p. 91–2° C | White crystals |
| 7 | CONHCH=CCl$_2$, OC(O)CH$_3$, Cl (phenyl) | m.p. 98–100° C | White crystals |
| 8 | CONHCH=CCl$_2$, OC(O)CH$_3$, Br (phenyl) | m.p. 133–4° C | White crystals |
| 9 | CONHCH=CCl$_2$, OC(O)C$_2$H$_5$ (phenyl) | m.p. 37–8° C | White crystals |
| 10 | CONHCH=CCl$_2$, OC(O)C$_3$H$_7$(n) (phenyl) | m.p. 124–5° C | White crystals |
| 11 | CONHCH=CCl$_2$, OC(O)C$_3$H$_7$(i) (phenyl) | m.p. 122–4° C | White crystals |

TABLE 1-continued

| Compound No. | Compound | M.P. or $n_D^{25}$ | Appearance |
|---|---|---|---|
| 12 | phenyl-CONHCH=CCl$_2$ with OC(O)C$_{11}$H$_{25}$(n) | m.p. 53–4° C | White crystals |
| 13 | phenyl-CONHCH=CCl$_2$ with OC(O)CH$_2$Cl | m.p. 93–5° C | White crystals |
| 14 | phenyl-CONHCH=CCl$_2$ with OC(O)CHCl$_2$ | m.p. 184–6° C | White crystals |
| 15 | phenyl-CONHCH=CCl$_2$ with OCH$_3$ | m.p. 111–2° C | White crystals |
| 16 | phenyl-CONHCH=CCl$_2$ with OC(O)OCH$_3$ | m.p. 72–3° C | White crystals |
| 17 | phenyl-CONHCH=CCl$_2$ with OC(O)OC$_2$H$_5$ | m.p. 70–2° C | White crystals |
| 18 | phenyl-CONHCH=CCl$_2$ with OC(O)OCH$_2$CH(CH$_3$)$_2$ | $n_D^{25}$ 1.5409 | Transparet liquid |
| 19 | phenyl-CONHCH=CCl$_2$ with OC(O)NHCH$_3$ | m.p. 98–101° C | White crystals |
| 20 | phenyl-CONHCH=CCl$_2$ with O$^-$Na$^+$ | m.p. 243° C (Decomposition) | Pale yellow crystals |
| 21 | Cl-phenyl-CONHCH=CCl$_2$ with O$^-$Na$^+$ | m.p. 280° C over | Pale yellow crystals |
| 22 | Br-phenyl-CONHCH=CCl$_2$ with O$^-$Na$^+$ | m.p. 280° C over | Pale yellow crystals |
| 23 | phenyl-CONHCH=CCl$_2$ with O$^-$H$^+$ | m.p. 174° C (Decomposition) | Pale yellow crystals |
| 24 | phenyl-CONHCH=CCl$_2$ with O$^-$(Zn$^{++}$)$_{\frac{1}{2}}$ | m.p. 158–160° C | White crystals |
| 25 | Br-phenyl-CONHCH=CCl$_2$ with O$^-$(Zn$^{++}$)$_{\frac{1}{2}}$ | m.p. 280° C over | White crystals |
| 26 | phenyl-CONHCH=CCl$_2$ with O$^-$(Cu$^{++}$)$_{\frac{1}{2}}$ | m.p. 135° C (Decomposition) | Pale green crystals |
| 27 | Br-phenyl-CONHCH=CCl$_2$ with O$^-$(Cu$^{++}$)$_{\frac{1}{2}}$ | m.p. 280° C over | Dark yellow green crystals |
| 28 | phenyl-CONHCH=CCl$_2$ with O$^-$(Mn$^{++}$)$_{\frac{1}{2}}$ | m.p. 191° C (Decomposition) | Yellow grey crystals |
| 29 | Br-phenyl-CONHCH=CCl$_2$ with O$^-$(Mn$^{++}$)$_{\frac{1}{2}}$ | m.p. 280° C over | Yellow grey crystals |
| 30 | Cl-phenyl-CONHCH=CCl$_2$ with O$^-$K$^+$ | m.p. 280° C over | Pale Yellow crystals |
| 31 | phenyl-CONHCH=CCl$_2$ with OH, NO$_2$ | m.p. 176–177° C | Pale yellow crystals |
| 32 | Cl,Cl-phenyl-CONHCH=CCl$_2$ with OC(O)CH$_3$ | m.p. 130–132° C | White crystals |
| 33 | Cl,Cl-phenyl-CONHCH=CCl$_2$ with ONa | m.p. 280° C over | Pale yellow crystals |
| 34 | Cl,Cl-phenyl-CONHCH=CCl$_2$ with OK | m.p. 280° C over | Pale yellow crystals |
| 35 | phenyl-CONHCH=CCl$_2$ with OC(O)CH$_3$, NO$_2$ | m.p. 109–112° C | Pale yellow crystals |
| 36 | Cl,Cl-phenyl-CONHCH=CCl$_2$ with OH | m.p. 173.5–174.0 | White crystals |

A preferred compound is a compound of the formula [I] where X represents hydrogen atom, chlorine atom, bromine atom, methyl group or nitro group, Y represents hydrogen atom, methyl atom, an alkylcarbonyl group where alkyl has from 1 to 3 carbon atoms or a metal atom of which the valence is 1 or 2, Z represents hydrogen atom or chlorine atom and n is 1.

The invention will first be described in connection with agricultural and horticultural uses.

The compounds of the invention, themselves, may be directly applied to said bacteria and fungi. However, in general, one or more of the compounds are mixed with suitable adjuvants and formed into bactericidal and fungicidal compositions such as an emulsifiable concentration, a wettable powder, a water-soluble concentration, an oil-soluble concentration, a dust, granules and pellets.

The amount of the compounds contained in the composition may be varied depending upon the method of application or kinds of crops of plant on which the composition is to be applied, but generally 1–95%, preferably 2 to 90%, by weight.

The adjuvants used in the present invention include all the substances other than effective compounds, which substances are added so as to enhance, maintain and increase the effect of power of the active compound or to dilute the concentration of the active compound. The adjuvants are, for example, various kinds of carriers and surface active agents. The carriers in the form of solid are, for example, clay, kaolin, talc, diatomaceous earth, silica, calcium carbonate or the like.

The carrier in the form of liquid are benzene, alcohols, acetone, xylene, methylnaphthalene, cyclohexanone, dimethylformamide, dimethylsulfoxide, animal and vegetable oils, fatty acids and their esters, various kinds of surfactants, etc.

It is also possible to enhance the effect by appropriately mixing the active compounds or the mixture of the compounds and carriers with auxiliary substances usually employed for agricultural preparations, such as an extending agent, an emulsifier, a wetting agent and a binding agent.

The present compounds may also be used in admixture with other agricultural fungicides, insecticides, herbicides, plant growth regulators, soil modifying agents or fertilizers. When the composition in the form of a wettable powder, a watersoluble concentration or an emulsifiable concentration is practically applied to bacteria or fungi which harm agricultural and horticultural plants or crops, it may preferably be diluted with water so that the present compounds are contained in an amount of about 30–8000 ppm, preferably 50–2000 ppm.

In the form of a dust, pellets or granules, the present compound is used in an amount of 0.03kg – 1kg/10 ares. For the soil treatment, preferably, the present compound is used in the form of a dust, granules or pellets and the compound preferably is applied in an amount of 0.05kg – 2kg/10 ares. When the compound is used for seed treatment, the seeds are dipped into the diluted solution in which the compound is contained in an amount of about 0.05 – 1.0% or seeds are dressed with a dust in which the compound is contained. The amount of the compound dressed is 0.1 – 5% of seed weight.

The representative plant diseases which are prevented by the application of the present compound are as follows:

1. Foliar treatment

Rice blast, the name of one of the most serious diseases of rice plant, caused by the fungus *Piricularia oryzae*, sheath blight of rice plant caused by *Corticium sasakii*, etc. downy mildew of cucumber caused by *Pseudoperonospora cubensis*, powdery mildew of cucumber caused by *Sphaerotheca fuliginea*, gray mold of tomato caused by *Botrytis cinerea*, cucumber scab caused by *Cladosporium cucumerinum*, anthracnose of cucumber caused by *Colletotrichum lagenarium*, etc.

Fruit crop diseases; black spot of Japanese pear caused by *Alternaria kikuchiana*, ripe rot of grape caused by *Glomerella cingulata*, brown rot of peach caused by *Sclerotinia laxa*, melanose of citrus tree caused by *Diaporthe ciyoi*, common green mold of citrus tree caused by *Penicillium digitatum*, penicillium rot of citrus tree caused by *penicillium fructigenum*, bacterial leaf blight of rice plant caused by *xanthomonas oryzae*, canker of citrus tree caused by *xanthomonas citri*, bacterial spot of cucumber caused by *pseudomonas lachrymans*, etc.

2. Soil treatment

Damping-off of cucumber, the name of a soil borne disease of cucumber, caused by the fungus *Pellicularia Filamentosa*, damping off of rice caused by *Fusarium sp* and *Rhizoctonia sp*, fusarium wilt of cucumber caused by *Fusarium oxysporum f, cucumerinum*, southern blight of pepper caused by *Corticium rolfsii*, verticilium wilt of eggplant caused by *Verticillium albo-atrum*, club root of cabbage caused by *Plasmodiophora brassicae*, etc.

3. Seed treatment

Seedling blight of rice plant caused by *Pellicularia filamentosa* and *Fusarium moniliforme*, cucumber scab caused by *Cladosporium cucumerinum*, damping-off of cucumber caused by *Pellicularia filamentosa*, etc.

The present invention will be explained more in detail by examples. Parts used in composition Examples are parts by weight.

Composition Example 1. Dust

Three (3) parts of N-(2',2'-dichlorovinyl)-salicylamide (compound No. 1), 48 parts of talc and 49 parts of clay were uniformly mixed and crushed to give a dust. The dust was sprayed over crops and plants, applied to soil and mixed with seeds and or tubers.

Composition Example 2. Wettable powder

Eighty (80) parts of O-acetyl-N-(2',2'-dichlorovinyl)-salicylamide (compound No. 6), 15 parts of kaolin, 3 parts of sodium alkylbenzenesulfonate and 2 parts of sodium polyacrylic acid were uniformly mixed and crushed to give a wettable powder. The wettable powder was suspended into water and used as spraying liquid.

Composition Example 3. Granules

Three (3) parts of sodium salt of N-(2',2'-dichlorovinyl)-salicylamide (compound No. 20), 35 parts of diatomaceous earth, 23 parts of bentonite, 37 parts of talc and 2 parts of disintegrator were uniformly mixed and 18 parts of water added. The mixture was blended to become uniformly wet and formed into granules by means of a granulating machine having a sieve of 0.6mm to 1.0mm and the wet granules were dried to obtain dry granules. The granules were sprayed to crops and plants and applied to soil.

Composition Example 4. Emulsifiable concentration

Twenty (20) parts of O-isobutoxy-N-(2',2'-dichlorovinyl) salicylamide (compound No. 23) were dissolved into 63 parts of xylene. Seventeen (17) parts of the condensation products of alkylphenol and ethylene oxide were dissolved in the resultant solution to obtain an emulsifiable concentration. The concentration was diluted with water to form emulsion and the emulison was used as spraying liquid. Then the effect of the present invention will now be explained by the following experimental examples.

Experimental Example 1.

Exterminating test on seedling blight of rice plant

Nursery boxes (60 × 30 × 3 cm) were filled with soil which were contaminated with pathogen (Fusarium sp. and Rhizoctonia sp.) The dust in which the present compound was contained in a ratio of 5% by weight was added in the box in a ratio of 5 grams per box and mixed well with soil. Thereafter, seeds of rice plant (variety: Nihonbare) were sowed in drills at a rate of 0.3 liter per box and grown up in a lighting chamber at 17° C. After 7 days from the sowing, the boxes were carried out in the field. Furthermore, 10 days thereafter the observations were made. Four percent (4%) dust of 3-hydroxy-5-methyl isoxazol (hereinafter referred to as hydroxyisoxazol) on the market was used as a control and tested by the same method. The test results are shown in Table 2 with a "percentage of healthy seedlings". The percentage of healthy seedlings was calculated as follows:

Table 2.

$$\text{Percentage of healthy seedlings} = \frac{\text{Number of healthy seedlings}}{\text{Number of observed seedlings}} \times 100$$

| Test compounds (Number) | Amount of treatment (a.i.)* | Percentage of healthy seedlings (%) | Phyto-toxicity |
|---|---|---|---|
| 1 | 0.25g/box | 80.2 | Nil |
| 2 | " | 72.4 | Nil |
| 3 | " | 65.3 | Nil |
| 4 | " | 76.6 | Nil |
| 5 | " | 62.0 | Nil |
| 6 | " | 83.2 | Nil |
| 7 | " | 70.2 | Nil |
| 8 | " | 71.3 | Nil |
| 9 | " | 69.8 | Nil |
| 10 | " | 72.1 | Nil |
| 11 | " | 68.7 | Nil |
| 12 | " | 65.0 | Nil |
| 13 | " | 62.0 | Nil |
| 14 | " | 70.8 | Nil |
| 15 | " | 70.2 | Nil |
| 16 | " | 71.5 | Nil |
| 17 | " | 68.3 | Nil |
| 18 | " | 72.1 | Nil |
| 19 | " | 64.7 | Nil |
| 20 | " | 74.9 | Nil |
| 21 | " | 70.7 | Nil |
| 22 | " | 69.9 | Nil |
| 23 | " | 70.8 | Nil |
| 24 | " | 71.3 | Nil |
| 28 | " | 73.0 | Nil |
| 29 | " | 69.8 | Nil |
| 30 | " | 71.4 | Nil |
| 31 | " | 70.2 | Nil |
| 32 | " | 69.8 | Nil |
| 33 | " | 70.4 | Nil |
| 34 | " | 72.2 | Nil |
| 35 | " | 71.2 | Nil |
| Control (Hydroxyisoxazol 4% dust) | 0.20g/box | 70.6 | Nil |
| Untreated | | 34.2 | — |

*Active Ingredient

Experimental Example 2

Exterminating test on cucumber scab

The cucumber seeds (variety: Sagamihanjiro) were sown in pots (diameter 18 cm). Eighty percent (80%) wettable powder (contents of active compound: 80%) of the present invention was diluted with water to obtain a suspension. The suspension was sprayed over the cucumber seedlings of the stage of 3-4 leaves in an amount of 20 ml per pot. After 24 hours, these pots were inoculated by means of spray of spore suspension of Cladosporium cucumerinum. The thus-inoculated seedlings were placed in a moist chamber at 20° C for 24 hours. The pots were continuously kept in a greenhouse at 20° C. The following wettable powders on the market were used as controls.

Control (1)

70% wettable powder of 1,2-bis (3-methoxy carbonyl-2-thioureid) benzene (hereinafter referred to as "thiophanate methyl") on the market.

Control (2)

75% wettable powder of ethylene bis (dithiocarbamic acid) manganese (hereinafter referred to as "maneb") on the market. After 5 days of the inoculation, degrees attached by the pathogen were observed and the results were shown in Table 3 with an "Infected Index". The "Infected Index" was calculated as follows:

$$\text{Infected Index} = \frac{(A \times 3) + (B \times 2) + (C \times 1)}{(A + B + C + D) \times 3} \times 100$$

A : Number of leaves which were killed by hard attack
B : Number of leaves severely attacked
C : Number of leaves slightly attacked
D : Number of healthy leaves

Table 3.

| Test compounds (Number) | Concentration (ppm) | Infected Index | Phyto-toxicity |
|---|---|---|---|
| 1 | 500 | 9.4 | Nil |
| 2 | " | 11.0 | Nil |
| 5 | " | 10.7 | Nil |
| 6 | " | 8.2 | Nil |
| 11 | " | 10.1 | Nil |
| 14 | " | 7.9 | Nil |
| 15 | " | 8.9 | Nil |
| 20 | " | 13.7 | Nil |
| 25 | " | 12.1 | Nil |
| Control (1) (Thiophanatemethyl 70% wettable powder) | 500 | 14.6 | Nil |
| Control (2) (Maneb 75% wettable powder) | 1,500 | 12.5 | Nil |
| Untreated | — | 91.0 | — |

Experimental Example 3.

Exterminating test on damping-off of cucumber

The pots (diameter, 12 cm) were filled with field soil and then soil infected by adding Rhizoctonia solani in an amount of 5 grams per pot uniformly into the pots. Thereafter, 10 seeds of cucumber (variety: Azumamidori) were sown in each pot.

Eighty percent (80%) wettable powder of the present invention was diluted with water to obtain a suspension and each pot was drenched with the suspension in an amount of 50 milliliters. Then, the pots were transferred to the greenhouse. Fifty percent (50%) wettable powder of pentachloronitro benzene (hereinafter referred to as PCNB) on the market was used as a control and tested by the same method. After 10 days of the inoculation, degrees attacked by the pathogen were observed and a "Percentage of healthy seedlings" was calculated. The "Percentage of healthy seedlings" was calculated as follows:

$$\text{Percentage of healthy seedlings} = \frac{\text{Number of healthy seedlings in treated pot}}{\text{Number of germination in untreated and uninfected pot}} \times 100$$

The results were shown in Table 4.

Table 4.

| compounds (Number) | Concentration (ppm) | Percentage of healthy seedlings (%) | Phytotoxicity |
|---|---|---|---|
| 1 | 1,000 | 100 | Nil |
| 2 | " | 95 | Nil |
| 3 | " | 70 | Nil |
| 4 | " | 90 | Nil |
| 5 | " | 80 | Nil |
| 6 | " | 100 | Nil |
| 8 | " | 75 | Nil |
| 9 | " | 90 | Nil |
| 10 | " | 100 | Nil |
| 11 | " | 100 | Nil |
| 12 | " | 70 | Nil |
| 13 | " | 100 | Nil |
| 14 | " | 95 | Nil |
| 15 | " | 60 | Nil |
| 16 | " | 100 | Nil |
| 17 | " | 85 | Nil |
| 18 | " | 100 | Nil |
| 19 | " | 65 | Nil |
| 20 | " | 100 | Nil |
| 21 | " | 80 | Nil |
| 22 | " | 75 | Nil |
| 23 | " | 100 | Nil |
| 24 | " | 100 | Nil |
| 25 | " | 80 | Nil |
| 26 | " | 100 | Nil |
| 27 | " | 85 | Nil |
| 28 | " | 100 | Nil |
| 29 | " | 55 | Nil |
| 30 | " | 70 | Nil |
| 31 | " | 85 | Nil |
| 32 | " | 75 | Nil |
| 33 | " | 90 | Nil |
| 34 | " | 65 | Nil |
| 35 | " | 95 | Nil |
| Control (PCNB 50% wettable powder) | " | 45 | Nil |
| Untreated (inoculated) | — | 0 | — |
| Untreated (non-inoculated) | — | 100 | — |

Experimental Example 4

Exterminating test on Fusarium wilt of cucumber Twenty (20) grams of infected soil was added uniformly into each pot which was filled with steam sterilized field soil, then 18 seeds of cucumber (variety; Tokiwazibai) were sowed in each pot. Eighty percent (80%) wettable powder of the present invention was diluted with water to obtain a suspension, and each pot was drenched with the suspension in an amount of 100 ml. Fifty percent (50%) wettable powder of methyl-1-(butylcarbamoyl) 2-benzimidazol carbamate (hereinafter referred to as Benlate) on the market was used as a control and tested by the same method. After two weeks of planting, degrees attacked by the pathogen was observed and a "percentage of healthy seedlings" was calculated as follows:

$$\text{Percentage of healthy seedlings} = \frac{\text{Number of healthy seedlings in treated pot}}{\text{Number of emerged seedlings in untreated and uninfected pot}}$$

The results are shown in Table 5

Table 5.

| Test Compounds (Number) | Concentration (ppm) | Percentage of healthy seedlings (%) | Phytotoxicity |
|---|---|---|---|
| 1 | 500 | 73.0 | Nil |
| 2 | " | 68.1 | Nil |
| 3 | " | 62.4 | Nil |
| 4 | " | 68.7 | Nil |
| 5 | " | 58.9 | Nil |
| 6 | " | 83.0 | Nil |
| 7 | " | 76.5 | Nil |
| 8 | " | 73.3 | Nil |
| 9 | " | 75.0 | Nil |
| 10 | " | 70.0 | Nil |
| 11 | " | 65.5 | Nil |
| 12 | " | 53.4 | Nil |
| 13 | " | 70.5 | Nil |
| 14 | " | 62.8 | Nil |
| 15 | " | 51.2 | Nil |
| 16 | " | 38.2 | Nil |
| 17 | " | 47.5 | Nil |
| 18 | " | 42.0 | Nil |
| 19 | " | 38.0 | Nil |
| 20 | " | 45.5 | Nil |
| 21 | " | 46.0 | Nil |
| 22 | " | 48.0 | Nil |
| 23 | " | 59.5 | Nil |
| 24 | " | 47.0 | Nil |
| 25 | " | 49.5 | Nil |
| 26 | " | 58.0 | Nil |
| 27 | " | 58.0 | Nil |
| 28 | " | 57.0 | Nil |
| 29 | " | 57.5 | Nil |
| 30 | " | 58.0 | Nil |
| 31 | " | 46.0 | Nil |
| 32 | " | 73.0 | Nil |
| 33 | " | 48.0 | Nil |
| 34 | " | 60.0 | Nil |
| 35 | " | 79.0 | Nil |
| Control (Benlate 50% wettable powder) | " | 45.0 | Nil |
| Untreated | — | 0 | — |

Experimental Example 5

Exterminating test on gray mold of tomato The seedlings of kidney beans (variety: Orient) of 5–6 leaves stage were employed in this test. Eighty percent (80%) wettable powder of the present invention was diluted with water and sprayed over the seedlings in an amount of 10 ml per pot. The leaves were cut from the plant at 24 hours after spraying, and placed in the petri dishes (12 cm in diameter). Thereafter disks (5 mm in diameter) were cut with a cork borer from potato dextrose agar on which the pathogen (*botrytis cinerea*) was cultured. The disks were placed on the leaves. The dishes were placed in such a moistural condition as to cause the pathogen to propagate. Thiophanate methyl 70% wettable powder on the market was used as a control and tested by the same method. After forty eight (48) hours after inoculation, diameters of the lesions were observed, and an "Effect Index" was calculated as follows;

$$\text{Effect Index} = \left(1 - \frac{\text{Lesion diameter in treated leaves}}{\text{Lesion diameter in untreated leaves}}\right) \times 100$$

The results are shown in Table 6.

Table 6

| Test Compound (Number) | Concentration (ppm) | Effect Index | Phytotoxicity |
|---|---|---|---|
| 1 | 1,000 | 84 | Nil |
| 2 | " | 79 | Nil |
| 6 | " | 75 | Nil |
| 10 | " | 88 | Nil |
| 11 | " | 81 | Nil |
| 20 | " | 85 | Nil |
| 21 | " | 80 | Nil |
| Control (Thiophanate-methyl 70% wettable powder) | 500 | 82 | Nil |
| Untreated | — | 0 | — |

Experimental Example 6

Exterminating test on citrus canker. 4-year-old summer orange seedlings, planted in unglazed pots having a diameter of 20 cm, were employed in this test. Eighty percent (80%) wettable powder of the present invention was diluted with water, and sprayed over the seedlings in an amount of 50 ml per pot. The leaves of the seedlings were inoculated *Xanthomonas citri* by means of a needle. After the inoculation, the seedlings were maintained in a moist chamber at 25° C for 24 hours. Then the pots were transferred into the greenhouse. Streptomycin 20% wettable powder was used as a control, and tested by the same method. After 2 weeks after the inoculation, degrees of disease attack were observed, and an "Effect Index" was calculated as follows:

$$\text{Effect Index} = \left(1 - \frac{\text{Attack rate in treated pot}}{\text{Attack rate in untreated pot}}\right) \times 100$$

where $$\text{Attack rate} = \frac{\begin{array}{l}\text{Number of leaves under slight attack} \times 1 \\ + \text{Number of leaves under medium attack} \times 2 \\ + \text{Number of leaves under severe attack} \times 3\end{array}}{\text{Total number of leaves tested} \times 3}$$

The results are shown in Table 7.

Table 7.

| Test compounds (Number) | Concentration (ppm) | Effect Index | Phytotoxicity |
|---|---|---|---|
| 1 | 1,000 | 95.8 | Nil |
| 2 | " | 99.3 | Nil |
| 3 | " | 81.0 | Nil |
| 5 | " | 98.2 | Nil |
| 6 | " | 96.1 | Nil |
| 13 | " | 67.3 | Nil |
| 14 | " | 73.2 | Nil |
| 17 | " | 68.3 | Nil |
| 21 | " | 77.0 | Nil |
| 22 | " | 49.8 | Nil |
| 23 | " | 41.5 | Nil |
| 25 | " | 80.6 | Nil |
| 26 | " | 47.5 | Nil |
| 28 | " | 73.6 | Nil |
| 29 | " | 56.2 | Nil |
| Control (Streptomycin 20% wettable powder) | 200 | 28.7 | Nil |
| Untreated | — | 0 | — |

Experimental Example 7

Exterminating test for seed treatment. Cucumber seeds (variety: Oyashima) were dipped in the spores suspension of *Cladosporium cucumerinum* and dried. After 1 day, the seeds were dressed with 80% wettable powder of the present invention. On the other hand, other seeds were dipped in the solution of 80% wettable powder of the present invention. Five (5) seeds treated by either dressing or dipping were placed on each potato dextrose agar plate. After 10 days after the treatment, degrees attacked by the pathogen were observed and the results were shown with an "Effective Index". An "Effective Index" was calculated as follows:

$$\text{Effective index} = \frac{\begin{array}{l}\text{Number of diseased seeds in untreated plot} \\ - \text{Number of diseased seeds in treated plot}\end{array}}{\text{Number of diseased seeds in untreated plot}} \times 100$$

The results are shown in Table 8.

Table 8

| Tested Compounds (Number) | Method of treatment | Concentration (and dipped time) | Effective Index | Phytotoxicity |
|---|---|---|---|---|
| 1 | dressed | 1 % | 87 | Nil |
| 6 | " | " | 95 | Nil |
| 20 | " | " | 90 | Nil |
| 1 | dipped | 5,000 ppm (30 min.) | 69 | Nil |
| 6 | " | " | 88 | Nil |
| " | " | " | 81 | Nil |
| Untreated | — | — | 0 | Nil |

The methods of the present invention also comprehend applying to industrial raw materials, industrial products and water in circulating water systems an effective amount of one or more compounds of formula (1). The bactericidal, fungicidal and algicidal compositions employed in such methods comprise 99.5%–5% by weight of a suitable adjuvant and 0.5–95% by weight of one or more compounds of formula (1).

The industrial raw materials and products to which such methods may be applied include organic matter: for example, cellulosic material such as wood, wooden articles, paper, cotton, fibers, textiles and bamboo, petroleum products such as plastics, plastic articles, oils and paints and leathers; inorganic matter such as metal articles; and products consisting of organic and inorganic matter such as ships and sheds for animals.

The term "circular water systems" means a system in which water is used many times by cycling. Such circulating water systems include, for example, the water systems in cooling towers for air conditioning, swimming pools, cooling equipments for reactors and the paper manufacturing industry.

Suitable adjuvants of the composition used in such methods of the present invention include, for example, carriers, extenders, emulsifying agents, wetting agents, fixing agents and surface active agents. The term "carrier" is used herein to mean a diluent or vehicle by which the active compound is brought into contact with bacteria, fungi and algae.

Solid carrier materials and liquid carrier materials are usually used as carriers in the present invention. Solid carrier materials include, for example, clay, kaolin, talc, diatomaceous-earth, silica and calcium carbonate. Liquid carrier materials include, for example, benzene, alcohol. acetone, xylene, methylnaphthalene, cyclohexanone, dimethylformamide, diethysulfoxide, animal and vegetable oils, fatty acids and ester thereof and various surface active agents.

The compounds of formula (1) have superior bactericidal, fungicidal and algicidal activity against bacteria, fungi and algae which propagate on industrial raw materials and industrial products and in water in circulating water systems and have no irritative or offensive odor and very low toxicity. The value of acute oral toxicity of the compounds of formula (1) against a mouse, which is represented by $LD_{50}$, is more than 6000 mg/kg in the case of N-($\beta,\beta$-dichlorovinyl) salicylamide and more than 1000 mg/kg in the case of other compounds of the formula (1). Accordingly, the compounds are safe to handle. Therefore, the compounds are used for controlling said bacteria, fungi and algae.

The compounds of the formula (I) of the present invention are prepared as follows:

N-($\beta,\beta$-dichlorovinyl) salicylamide is prepared by heating chloral with salicylamide, followed by treatment with a mixture of zinc and acetic acid.

A metallic salt of N-(β,β-dichlorovinyl) salicylamide is prepared by reacting a hydroxylmetal compound such as sodium hydroxide with N-(β,β-dichlorovinyl) salicylamide. The compounds of the formula

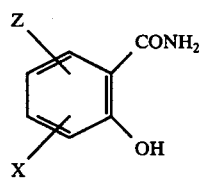
(II)

wherein X and Z are defined as above are condensed with chloral by a method similar to that shown in U.S.P. at No. 2,936,323. The products of the condensation are compounds of the formula

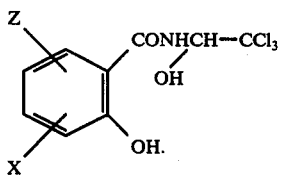
(III)

These compounds are reduced with a reductant such as zinc in a suitable solvent such as acetic acid, methanol or ethanol at a temperature between room temperature and 120° C. Compounds of the formula

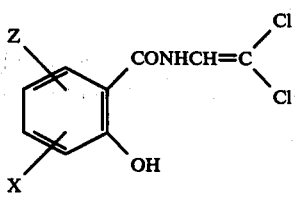
(IV)

are obtained by the said reduction. The compound of the formula (IV) is reacted with equivalent mole to 2 time moles of an alkali halide, an acyl chloride, an alkoxycarbonyl chloride or an alkyl isocyanate in the presence of a suitable base such as trimethylamine and triethylamine in an inactive solvent at a temperature of 5° C to 120° C to obtain the compound

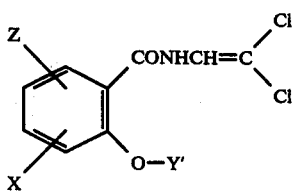
(V)

wherein Y' represents methyl group, an alkycarbonyl group where the alkyl group has from 1 to 12 carbon atoms and may be substituted by one or more halogen atoms, a lower alkoxy carbonyl group, a lower alkyl amino carbonyl group, and X and Z are defined as above.

The alkyl halide is, for example, methyl iodide, ethyl iodide or propyl chlorine. The acyl chloride where alkyl group may be substituted halogen atoms is, for example, acetyl chloride, chloroacetylchloride, dichloroacetyl chloride, propionyl chloride, butyryl chloride, isobutyryl chloride or lauroyl chloride. The alkoxy carbonyl chloride is, for example, methyl chloroformate, ethyl chloroformate or propyl chloroformate. The alkyl isocyanate is, for example, methyl isocyanate or propyl isocyanate.

The compound of the formula (IV) is reacted with equivalent of an alkali metal hydroxide in water at room temperature to obtain the formula

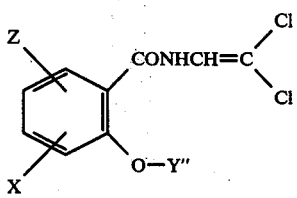
(VI)

wherein Y" represents alkali metal such as sodium atom or potassium atom.

The alkali metal hydroxide is, for example, sodium hydroxide or potassium hydroxide.

The compound of the formula (IV) is reacted with equivalent of a metal halide except alkali metal halide, a metal acetate or a metal sulfate in the presence of alkali metal hydroxide such as sodium hydroxide or potassium hydroxide in water at room temperature to obtain the formula

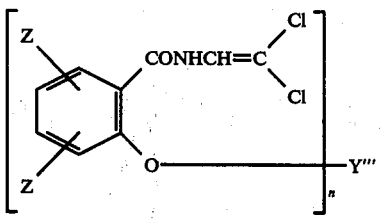

wherein Y''' represents metal atom except alkali metal atom and n represents 1 or 2.

The metal halide is, for example, zinc chloride or manganous chloride. The metal acetate is, for example, zinc acetate or copper (II) acetate. The metal sulfate is, for example, copper sulfate.

In order to control the growth of said bacteria, fungi and algae with the compounds of the present ivention, the compounds are applied to industrial raw materials, industrial products and said water.

The compounds, themselves, may be directly applied to said materials, products and water. However, in general, one or more of the compounds are mixed with suitable adjuvants and formed into bactericidal fungicidal and algicidal compositions such as emulsifiable concentrate, wettable powder, water soluble concentrate, oil soluble concentrate, dust, granules or pellets.

The bactericidal, fungicidal and algicidal composition which contains the compounds of the present invention comprises about 0.05 to 95, preferably, 2 to 70 weight percent of the compounds and about 99.5 to 5, preferably, 98 to 30 weight percent of one or more suitable adjuvants.

In the case of treatment of industrial raw materials or products such as wood, wooden articles, fibers, textiles, paper, leathers, inside of sheds for animals, etc., usually their surfaces are treated with 0.1 – 10 g/m² of the compound in the form of a composition by means of spraying, coating or infiltrating.

In the case of treatment of industrial raw materials or products such as paints, adhesives and pastes, etc., usually the compound in the form of a composition is added to them and mixed. The amount of the compound added is usually about 0.01 to 0.1 percent by weight.

The growth of bacteria, fungi and algae on the bottom of ships can be prevented by coating the bottom with the paint containing the compound.

In the case of treatment of water in circulating water systems, the active compound is added to the water and the amount of the active compound is usually about 2 to 50 ppm, preferably about 10 to 30 ppm. The industrial raw materials and products which are most suitable to be treated with the active compounds are organic matter.

EXAMPLE 1.

Preparation of N-($\beta,\beta$-dichlorovinyl) salicylamide (Compound No. 1):

The mixture of 27.4 g (0.2 mole) of salicylamide and 32.45 g (0.22 mole) of chloral was heated at 90°-100° C for 5 hours. The reaction product was washed with water and dried. Fifty-six point nine (56.9) g of chloralsalicylamide (white crystals, m.p. 132°-133° C) were obtained.

Twenty eight point five (28.5) g (0.1 mole) of chloralsalicylamide were mixed with 150 ml of acetic acid. Then 26 g (0.4 mole) of zinc powder were added to this solution under agitation below 50° C. After agitation was continued for 30 minutes at 70°-80° C, the reaction mixture was cooled at room temperature and filtrated. Water was added to the filtrate to precipitate the crystals of the reaction product. The crystals were separated by filtration, washed with water and dried.

The yields of N-($\beta,\beta$-dichlorovinyl) salicylamide (white crystals, m.p. 187°-189° C) were 15.1 g (70%).
Analysis of elements:
Calculated; C: 46.58%, H: 3.04%, N: 6.04%; Found; C: 46.57%, H: 2.87%, N: 6.22%; as $C_9 H_7 N O_2 Cl_2$.

EXAMPLE 2

Preparation of N-(2',2'-dichlorovinyl)-5-chlorosalicylamide (Compound No. 2)

Thirty (30) g (0.09 mol) of N-(1'-hydroxy-2',2',2'-trichloroethyl)-5-chlorosalicylamide were dissolved in 150 ml of acetic acid. Nine point two (9.2) g (0.14 mol) of zinc powder were added into the solution under stirring at the temperature from 20° C to 40° C and the reaction was continued for 4 hours at the same temperature. The temperature was finally raised at 80° C and then excess zinc was removed by filtration. The filtrate was cooled to obtain 28g of crystals of N-(2',2'-dichlorovinyl)5-chloro salicylamide was obtained. Melting point of it was 208° C–210° C.
Elemental analysis for $C_9H_6Cl_3NO_2$
Calculation: C: 40.56%, H: 2.27%, N: 5.26%; Found: C: 40.37%, H: 2.23%, N: 5.65%;

EXAMPLE 3

Preparation of O-acetyl-N-(2,2-dichlorovinyl) salicylamide (Compound No. 6)

One hundred and fifty (150) g (0.65 mol) of N-(2,2-dichlorovinyl) salicylamide was suspended into 450 ml of benzene. Two hundred (200) g (1.95 mol) of acetic anhydride was added into the suspension with stirring. After 10 g (0.13 mol) of pyridine was added dropwise to the solution at 30° C – 40 ° C, the mixture was refluxed for 5 hours. After cooling, the reaction mixture was washed with water and an agueous solution of 5%-sodium hydrogencarbonate, and again with water. Then the reaction mixture was condenced under the reduced pressure to obtain a solid matter. The solid matter was recrystallized from cyclohexane. One hundred and seventy (170) g of O-acetyl-N-(2,2-dichlorovinyl) salicylamide, mp. 91°–92° C, was obtained.
Elemental analysis for $C_{11}H_9Cl_2NO_3$
Calculation: C: 48.20%, H: 3.31%, N: 5.11%; Found: C: 48.30%, H: 3.06%, N: 5.08%

EXAMPLE 4

Preparation of O-methoxycarbonyl-N-(2,2-dichlorovinyl) salicylamide (Compound No. 16)

Twenty (20) g (0.09 mol) of N-(2,2-dichlorovinyl) salicylamide were dissolved into 100 ml of benzene. Eight point one (8.1) g (0.09 mol) of methyl chloroformate were added to the solution with stirring. After 9 g (0.09 mol) of triethylamine were added dropwise under 10° C the mixture was reacted for 3 hours at the room temperature and refluxed for 30 minutes to complete the reaction. After cooling, the reaction mixture was washed with water, an aqueous solution of 5%-sodium hydrogencarbonate, and finally with water to obtain the neutral reaction mixture. The neutral reaction mixture was concentrated under reduced pressure to obtain a solid matter. The solid matter was recrystallized from methanol. Twenty two point five (22.5) g of O-(N'-methoxy carbamoyl)-N-(2,2-dichlorovinyl) salicylamide, mp. 72°–73° C, was obtained.
Elemental analysis for $C_{11}H_9Cl_2NO_4$
Calculation: C: 45.54%, H: 3.13%, N: 4.83% Found: C: 45.30%, H: 3.10%, N: 4.61%

EXAMPLE 5

Preparation of O-(N'-methylcarbamoyl)-N-(2,2-dichlorovinyl) salicylamide (Compound No. 19)

Twelve (12) g (0.05 mol) of (N-(2,2-dichlorovinyl) salicylamide were dissolved in 100ml of benzene and 4 g (0.07 mol) of methyl isocyanate were added with stirring at below 10° C. Six point six (6.6) g (0.07 mol) of tirethylamine were added dropwise to the solution. The mixture was reacted for 3 hours at room temperature and refluxed for 30 minutes. The reaction mixture was cooled and washed with water, then an aqueous solution of 5%– sodium hydrocarbonate and finally water to obtain the neutral reaction mixture. The neutral reaction mixture was concentrated to obtain a solid matter under the reduced pressure. The solid matter was recrystallized from methanol. Thirteen point five (13.5) g of O-(N'-methylcarbamoyl)-N-(2,2-dichlorovinyl) salicylamide (mp. 98°–101° C) were obtained.
Elemental analysis for $C_{11}H_{10}Cl_2N_2O_3$
Calculated: C: 45.70%, H: 3.49%, N: 9.69% Found: C: 45.81%, H: 3.45%, N: 9.60%

EXAMPLE 6

Preparation of O-acetyl-N-(2',2'-dichlorovinyl)-5-chlorosalicylamide (Compound No. 7)

Five (5) g (0.018 mol) of N-(2',2'-dichlorovinyl)-5-chlorosalicylamide were dissolved in 30 ml of benzene, and 2.2g (0.022 mol) of acetic anhydride and a few drops of pyridine were added with stirring. The mixture was stirred for 4 hours at 50° C. The reaction mixture was washed with water, an aqueous solution of 5%- sodium hydrocarbonate and water, successively. The reaction mixture was concentrated under the reduced pressure to obtain a solid matter. The solid matter was recrystallized from benzene. Four (4) g of O-acetyl-N-(2',2'-dichlorovinyl)-5-chlorosalicylamide, mp. 98°–100° C, were obtained.

Elemental analysis for $C_{11}H_7Cl_3NO_3$

Calculation: C: 42.82%, H: 2.61%, N: 4.54% Found: C: 42.65%, H: 2.70%, N: 4.41%

EXAMPLE 7

The preparation of sodium salt of N-($\beta,\beta$-dichlorovinyl) salicylamide (Compound No. 20):

Two hundred thirty two (232) g (1 mol) of N-($\beta,\beta$-dichlorovinyl) salicylamide were added under agitation to the aqueous solution wherein 43g (1 mole) of 93%-sodium hydroxide were dissolved in 300 ml of water and then agitated at room temperature for 3 hours.

Water was evaporated under reduced pressure. The yields of sodium salf of N-($\beta,\beta$-dichlorovinyl) salicylamide was 225g. The sodium salt was pale light brown crystals and decomposed at 243° C Analysis of elements:

Calculated: C: 42.55%, H: 2.38%, N: 5.51%; Found: C: 42.32%, H: 2.40%, N: 5.40%; as $C_9H_6Cl_2NO_2Na$ The following metallic salts were prepared by the same method as the sodium salts.

Table 2

| Compound No. | Melting Point Metallic Salt | (° C) | Appearance |
|---|---|---|---|
| 23 | Potassium salt | 243 (Decomposition) | Pale light brown crystals |
| 24 | Zinc salt | 158–160 | White crystals |
| 26 | Cupric salt | 135 (Decomposition) | Pale green crystals |
| 28 | Manganous salt | 191 (Decomposition) | Yellow grey crystals |

EXAMPLE 8

The preparation of sodium salt of N-(2'-2'-dichlorovinyl)-5-chlorosalicylamide (Compound No. 21)

Five (5) g (0.019 mol) of N-(2',2'-dichlorovinyl)-5-chlorosalicylamide were added under agitation to the aqueous solution wherein 0.7 g (0.019 mol) of 93%-sodium hydroxide were dissolved in 30 ml of water and then agitated at room temperature for 1 hour.

Water was evaporated under reduced pressure. The yields of sodium salt of N-(2',2'-dichlorovinyl)-5-chlorosalicylamide was 5.4. The sodium salt was pale light brown crystals and melting point of it was over 280° C.

Elemental analysis as $C_9H_5Cl_3NO_2Na_5$

Calculated: C: 37.47%, H: 1.75%, N: 4.86%; Found: C: 37.33%, H: 1.73%, N: 4.79%;

EXAMPLE 9

The compounds shown in Table 9 were prepared.

Table 9

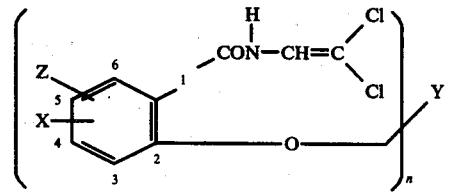

| Compound No. | X and position of | Y | Z | n | M.P.(° C) or $n_D^{25}$ | Appearance | Method of the preparation | A material compound corresponding to Y group |
|---|---|---|---|---|---|---|---|---|
| 22 | 5-Br | Na | H | 1 | Over 280 | Pale brown crystals | Similar method to Example 8 N-(2',2'-dichlorovinyl)-5-bromosalicylamido was reacted with equivalent of Zncl₂ in the presence of NaOH in water at room temperature. | NaOH |
| 25 | 5-Br | Zn | H | 2 | " | White crystals | | ZnCl₂ |
| 27 | 5-Br | Cu (II) | H | 2 | " | Dark yellow green crystals | Similar method to the preparation of compound No. 25 | CuSO₄ |
| 29 | 5-Br | Mu (II) | H | 2 | " | Yellow grey crystals | " | MnCl₂ |
| 5 | 4-CH₃ | H | H | 1 | m.p. 189–191 | White crystals | Similar method to Example 2 | |
| 4 | 3-CH₃ | H | H | 1 | m.p. 78–82 | White crystals | " | |
| 3 | 5-Br | H | H | 1 | m.p. 204 | White crystals | " | |
| 31 | 3-NO₂ | H | H | 1 | m.p. 176–177 | Pale yellow crystals | Nitration of N-(2,2-dichlorovinyl) salicylamide with equivalent mole of nitric acid in the presence of acetic acid at room temperature. | |

Table 9-continued

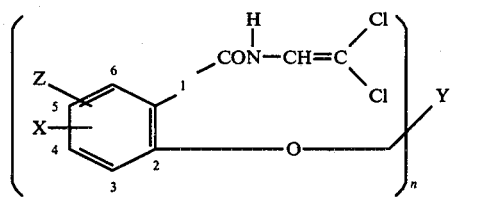

| Compound No. | X and position of | Y | Z | n | M.P.(° C) or $n_D^{25}$ | Appearance | Method of the preparation | A material compound corresponding to Y group |
|---|---|---|---|---|---|---|---|---|
| 9 | H | C(O)C₂H₅ | H | 1 | m.p. 37–38 | White crystals | Similar method to Example 3 | ClC(O)C₂H₅ |
| 10 | H | C(O)C₃H₇(n) | H | 1 | m.p. 124–125 | White crystals | " | ClC(O)C₃H₇(n) |
| 11 | H | C(O)C₃H₇(i) | H | 1 | m.p. 122–124 | White crystals | " | ClC(O)C₃H₇(i) |
| 12 | H | C(O)C₁₁H₂₃(n) | H | 1 | m.p. 53–59 | White crystals | " | ClC(O)C₁₁H₂₃(n) |
| 13 | H | C(O)CH₂Cl | H | 1 | m.p. 93–95 | White crystals | Similar method to Example 3 | ClC(O)CH₂Cl |
| 14 | H | C(O)CHCl₂ | H | 1 | m.p. 184–186 | White crystals | " | ClC(O)CHCl₂ |
| 8 | 5-Br | C(O)CH₃ | H | 1 | m.p. 133–134 | White crystals | Similar method to Example 6 | ClC(O)CH₃ |
| 17 | H | C(O)OC₂H₅ | H | 1 | m.p. 70–72 | White crystals | Similar method to Example 4 | ClCOOC₂H₅ |
| 18 | H | C(O)OCH₂CH(CH₃)CH₃ | H | 1 | $n_D^{25}$ 1.5409 | Transparet liquid | " | ClCOOCH₂CH(CH₃)CH₃ |
| 15 | H | CH₃ | H | 1 | m.p. 111–112 | White crystals | Alkylation of N-(2,2-dichlorovinyl) salicylamide with methyl iodide | CH₃I |
| 30 | 5-Cl | K | H | 1 | m.p. over 280 | Pale Yellow crystals | Similar method to Example 8 | KOH |
| 36 | 3-Cl | H | 5-Cl | 1 | m.p. 173.5–174.0 | White crystals | Similar method to Example 2 | |
| 32 | 3-Cl | C(O)CH₃ | 5-Cl | 1 | m.p. 130–132 | White crystals | Similar method to Example 6 | ClC(O)CH₃ |
| 33 | 3-Cl | Na | 5-Cl | 1 | m.p. over 280 | Pale yellow crystals | Similar method to Example 8 | NaOH |
| 34 | 3-Cl | K | 5-Cl | 1 | m.p. over 280 | Pale yellow crystals | " | KOH |
| 35 | 3-NO₂ | C(O)CH₃ | H | 1 | m.p. 109–112 | Pale yellow crystals | Similar method to Example 6 | ClC(O)CH₃ |

The following are some illustrative examples which exhibit an excellent antimicrobial and algicidal effect of the present invention and some examples of compositions of compositions of the present invention. All parts are by weight.

EXAMPLE 10

An emulsifiable concentrate was prepared as follows:

| | |
|---|---|
| Compound No.1 | 10 parts |
| Isophorone | 40 parts |
| Xylene | 31 parts |
| Dimethylformamide | 7 parts |
| Surface active agents | 12 parts |

The above ingredients were blended. An emulsifiable concentrate was obtained. Before application, the emulsifiable concentrate was diluted with water up to 400–2000 times and an emulsion was formed. Woods and fibers were soaked in the emulsion to control bacteria and fungi which propagate on them.

An emulsifiable concentrate containing compound No. 20, No. 23, No. 24, No. 26 or No. 28 was prepared by the same method as mentioned above.

EXAMPLE 11

An oil soluble concentrate was prepared as follows:

| | |
|---|---|
| Compound No.1 | 20 parts |
| Ethyl cellosolve | 40 parts |
| Dimethylformamide | 10 parts |
| Xylene | 30 parts |

The above ingredients were mixed. An oil soluble concentrate was obtained. In the form of the oil soluble concentrate, Compound No. 1 was added to paints or the cutting oil in an amount of 0.1%.

The growth of fungi in the paints or the cutting oil was controlled.

EXAMPLE 12

A wettable powder was prepared as follows:

| | |
|---|---|
| Compound No. 23 | 55 parts |
| Polyethyleneoxide | 3 parts | compound found to produce 100% control of the test bacteria and fungi).

Table 4.

| | Active Compounds | No. 1 | | No. 20 | | No. 23 | | No. 24 | | No. 26 | | No. 38 | |
|---|---|---|---|---|---|---|---|---|---|---|---|---|---|
| | Method of Examination | (1) | (2) | (1) | (3) | (1) | (3) | (1) | (3) | (1) | (3) | (1) | (3) |
| FUNGI | Aspergillus niger | 10 | 10 | 10 | — | 10 | — | 10 | — | 10 | — | 10 | — |
| | Penicillium Citrinum | 10 | 20 | 10 | — | 10 | — | 10 | — | 10 | — | 10 | — |
| | Cladosporium harbarum | 10 | 5 | 2.5 | — | 5 | — | 2.5 | — | 5 | — | 5 | — |
| | Chaetomium globosum | 5 | 10 | — | — | — | — | — | — | — | — | — | — |
| | Geotrichum candium | 10 | 20 | — | — | — | — | — | — | — | — | — | — |
| BAC-TERIA | Bacillus subtilis | 2.5 | 5 | — | 5 | — | 5 | — | 2.5 | — | 5 | — | 5 |
| | Staphylococcus aureus | 2.5 | 2.5 | 6 | 5 | — | 10 | — | 5 | — | 5 | — | 5 |
| | Escherichia coli | 80 | 80 | — | 60 | — | 60 | — | 40 | — | 60 | — | 60 |
| | Pseudomonas fluorescens | 40 | 40 | — | — | 13 | — | — | — | — | — | — | — |

| | |
|---|---|
| Ligninsulfonic acid | 5 parts |
| Diatom earth | 20 parts |
| Clay | 17 parts |

The above ingredients were blended. A wettable powder was obtained. Before application, the wettable powder was suspended in water. The resultant suspension was sprayed on the inside of sheds for animals by a sprayer to prevent the growth of fungi and bacteria in sheds for animals.

EXAMPLE 13

A water soluble concentrate was prepared as follows:

| | |
|---|---|
| Compound No. 20 | 10 parts |
| Ethyl cellosolve | 40 parts |
| Isophoron | 38 parts |
| Polyethyleneoxide | 10 parts |
| Alkylbenzenesulfonic acid | 2 parts |

The above ingredients were mixed. A water soluble concentrate was obtained.

Before application, the concentrate was diluted 500–1000 times with water and sprayed on the inside of cotes to prevent the growth of bacterial and fungi.

The solution was added to water in circular water systems to inhibit the growth of slime. The concentration of Compound No. 20 in the water was 10–20 ppm.

An amount from 0.01%–0.1% of Compound No. 20 as the solution was added to pastes or binding agents to prevent rottenness of them.

Bacteria, fungi and slime were inhibited for a long time.

EXAMPLE 14

Bacteriocidal activity and fungicidal activity of the active compounds of the present invention were examined by [1] potato-dextrose agar dilution method, [2] waxman's liquid medium dilution method or [3] glucose bouillon medium dilution method. The results are shown in Table 4 below as the minimum inhibitory concentration (the minimum concentration of active

EXAMPLE 15

Thirty grams (30g) of milk casein, 270ml of distilled water and 1 ml of 28% ammonia aqueous solution were mixed. A casein solution was obtained. Five milliliters (5 ml) of rotten casein solution were added to the casein solution obtained. The water soluble concentrate, which was obtained by Example 4 and contained Compound No. 1, was added to the resultant casein solution. The casein solution maintained at 30° C. The degree of rottenness of the casein solution was examined on 10th day, 20th day, and 30th day.

The results are shown in Table 5.

Table 5.

| Amount of compound No. 1 in the casein solution | 10th day | 20th day | 30th day |
|---|---|---|---|
| 0 (No treatment) | Rottenness and yellow coloration | Rottenness and yellow coloration | Rottenness and yellow coloration |
| 0.05 % | No rottenness | No rottenness | Slight rottenness |
| 0.1 % | No rottenness | No rottenness | No rottenness |

EXAMPLE 16

The emulsifiable concentrate which was prepared by Example 10 and which contained 10% of Compound No. 1 was entered to three vessels. These emulsifiable concentrates were diluted with water 500 times, 1000 times and 2000 times respectively. Emulsions were obtained. Each of silk, cotton and vinylon clothes was dipped into the three different concentrations of emulsions for 3 minutes and dried for 24 hours at room temperature. The clothes dreid were cut into a square of which a side was 1 cm long.

Test bacteria and fungi were inoculated on the whole surfaces of the plates of potato-dextrose agar medium. The square clothes were placed on the plates of agar culture medium of potato. The inoculated bacteria and fungi were incubated at 28° C for 4 days. The width of zones in which the growth of the test bateria and fungi was inhibited in the environment of the clothes was measured. The results are shown in Table 6.

Table 6

Test bacteria and fungi

| Clothes | Concentrate of Compound (%) No. 1 | The width of growth inhibition zones(mm) | | | |
|---|---|---|---|---|---|
| | | Bacteria | | Fungi | |
| | | Bacillus subtilis | Staphylococcus aureus | Aspergillus niger | Penicillium citrenum |
| Silk | Control | 0 | 0 | 0 | 0 |
| | 0.005 | 3 | 5 | 5 | 4 |
| | 0.01 | 6 | 8 | 7 | 6 |
| | 0.02 | 10 | 12 | 8 | 7 |
| Cotton | Control | 0 | 0 | 0 | 0 |
| | 0.005 | 3 | 5 | 6 | 5 |
| | 0.01 | 6 | 9 | 8 | 7 |
| | 0.02 | 10 | 13 | 11 | 9 |
| Vinylon | Control | 0 | 0 | 0 | 0 |
| | 0.005 | 2 | 4 | 4 | 3 |
| | 0.01 | 5 | 7 | 6 | 5 |
| | 0.02 | 9 | 11 | 8 | 7 |

EXAMPLE 17

The emulsifiable concentrates which were prepared by Example 10 were diluted with water 400 times and 800 times to form emulsions.

The square plates of beach of which a side was 5 cm long and thickness was 5 mm were dipped into the emulsion for 2 minutes and dried for 24 hours at room temperature.

The square plates were placed on the surface of agar plates. The suspensions which contained spores of Aspergillus niger, Penicillium citrinum, Cladosporium harbarum and chaetomium globosum were respectively sprayed on the agar plates and the square plates.

The test fungi were cultivated in the incubator at the humidity of 95% and the temperature of 28° C for 2 weeks.

The results are shown in Table 7. The degree of growth inhibition is defined in terms of the following numerical ratings.

Table 7

| Active Compound No. | Concentrate of active Compound | | |
|---|---|---|---|
| | The degree of growth inhibition | | |
| | 0.025% | 0.0125% | (No treatment) 0% |
| 20 | 3 | 3 | 1 |
| 23 | 3 | 3 | 1 |
| 24 | 3 | 3 | 1 |
| 26 | 3 | 3 | 1 |
| 28 | 3 | 3 | 1 |

EXAMPLE 18

The emulsifiable concentrates which were prepared by Example 10 were diluted with water 1000 times to form an emulsion.

A cloth of cotton was soaked into each emulsion for 2 minutes. The clothes were dried at room temperature and cut into a square of which a side was 1 cm long. Each kind of test bacteria and fungi was inoculated, separately on plates of potato-agar and one square cloth was placed on each of such plates. Test bacteria and fungi were cultivated at 28° C for 4 days. The width of the region of growth-inhibition which was formed a circumference of the cloth was examined. The results are shown in Table 8.

Table 8

| Compound Number | The width of the growth inhibition zone (mm) | | | |
|---|---|---|---|---|
| | Fungi | | Bacteria | |
| | Aspergillus niger | Penicillium citrinum | Bacillus subtilis | Staphylococcus aureus |
| 20 | 6 | 7 | 8 | 7 |
| 24 | 5 | 5 | 10 | 8 |
| No treatment | 0 | 0 | 0 | 0 |

EXAMPLE 19

Zero point zero two (0.02) part of active compounds in the form of 10% water soluble concentrate which was prepared by Example 13 was added into 100 parts of Waxman's liquid medium. Pieces of wood and iron (hereafter referred to as the slime test boards) were soaked into the Waxman's liquid medium. The bacteria which were gathered from circular water system were inoculated upon the Waxman's liquid medium and incubated at 27° C-34° C by shaking culture. The degree of propagation of the bacteria on the slime test boards was examined.

The growth-inhibiting activity of active compounds against the fungi and the green algae was also examined by the same method as mentioned above.

The results are shown in Table 9.

The degree of propagation of the bacteria, fungi or green algae on the slime test boards is defined in terms of the following symbols.

Table 9

| | Active Compound Number | Degree of propagation | | |
|---|---|---|---|---|
| | | 7th day | 14th day | 21st day |
| Bacteria | 20 | − | − | − |
| | 23 | − | − | + |
| | No treatment | ++ | +++ | ++++ |
| Fungi | 20 | − | − | − |
| | 23 | − | − | − |
| | No treatment | ++ | +++ | ++++ |
| Green algae | 20 | − | − | − |
| | 23 | − | − | + |
| | No treatment | ++ | +++ | ++++ |

− : no propagation
+ : the area of propagation is 1 − 25% on the slime test boards.
++ : the area of propagation is 26 − 50% on the slime test boards.
+++ : the area of propagation is 51 − 75% on the slime test boards.
++++ : the area of propagation is 76 − 100% on the slime test boards.

EXAMPLE 20

An emulsifiable concentrate was prepared as follows:

| | |
|---|---|
| Compound No. 2 | 10 parts |
| Isophorone | 40 parts |
| Xylene | 31 parts |
| Dimethylformamide | 7 parts |
| Surface active agents | 12 parts |

The above ingredients were blended. An emulsifiable concentrate was obtained. Before application, the emulsifiable concentrate was diluted with water up to 400–2000 times and an emulsion was formed. Wo ds and fibers were soaked in the emulsion to cotrol bacteria and fungi which propagate on them.

An emulsifiable concentrate containing compound No. 6, No. 7, No. 25, No. 3, No. 9, No. 10, No. 13, No. 17, No. 29 or No. 18 was prepared by the same method as mentioned above.

EXAMPLE 21

An oil soluble concentrate was prepared as follows:

| | |
|---|---|
| Compound No. 9 | 20 parts |
| Ethyl cellosolve | 40 parts |
| Dimethylformamide | 10 parts |
| Xylene | 30 parts |

The above ingredients were mixed. An oil soluble concentrate was obtained. In the form of the oil soluble concentrate, Compound No. 9 was added to paints or the cutting oil in an amount of 0.1%.

EXAMPLE 22

A wettable powder was prepared as follows:

| | |
|---|---|
| Compound No. 7 | 55 parts |
| Polyethyleneoxide | 3 parts |
| Ligninsulfonic acid | 5 parts |
| Diatom earth | 20 parts |
| Clay | 17 parts |

The above ingredients were blended. A wettable powder was obtained. Before application, the wettable powder was suspended in water. The resultant suspension was sprayed on the inside of sheds for animals by a sprayer to prevent the growth of fungi and bacteria in sheds for animals.

EXAMPLE 23

A water soluble concentrate was prepared as follows:

| | |
|---|---|
| Compound No. 21 | 10 parts |
| Ethyl cellosolve | 40 parts |
| Isophoron | 38 parts |
| Polyethyleneoxide | 10 parts |
| Alkylbenzenesulfonic acid | 2 parts |

The above ingredients were mixed. A water soluble concentrate was obtained. A water soluble concentrate containing Compound No. 2, No. 6, No. 7, No. 25, No. 10, No. 13 or No. 13 or No. 17 was prepared by the same method as mentioned above.

Before application, the concentrate was diluted 500–1000 times with water and sprayed on the inside of cotes to prevent the growth of bacteria and fungi.

The solution was added to water in circular water systems to inhibit the growth of slime. The concentration of Compound No. 21 in the water was 10–20 ppm.

An amount of 0.01–0.1% of Compound No. 21 as the solution was added to pastes or binding agents to prevent rottenness of them.

Bacteria, fungi and slime were inhibited for a long time.

EXAMPLE 24

Bactericidal activity and fungicidal activity of the active compounds of the present invention were examined by [1] potato-dextrose agar dilution method, or [2] glucose bouillon medium dilution method. The results are shown in Table 10 below as the minimum inhibitory concentration (the minimum concentration of active compound found to produce 100% control of the test bacteria and fungi).

Table 10

| Method | Minimum inhibitory amount (mcg/ml) | | | | | |
|---|---|---|---|---|---|---|
| | (1) | | | (2) | | |
| Active Compound No. / Bacteria and Fungi | Aspergillus niger | Penicillium citrinum | Cladosporium harbarum | Bacillus subtilis | Staphylococcus aureus | Escherichia coli |
| 2 | 10 | 10 | 5 | 5 | 5 | 60 |
| 6 | 10 | 10 | 5 | 2.5 | 5 | 40 |
| 16 | 10 | 20 | 10 | 10 | 10 | 60 |
| 19 | 20 | 10 | 5 | 10 | 10 | 60 |
| 7 | 2.5 | 2.5 | 2.5 | 1.3 | 1.3 | 10 |
| 21 | 10 | 5 | 5 | 2.5 | 2.5 | 40 |
| 25 | 20 | 20 | 10 | 5 | 5 | 60 |
| 29 | 20 | 20 | 10 | 5 | 10 | 60 |
| 4 | 20 | 20 | 20 | 10 | 10 | 80 |
| 3 | 20 | 10 | 10 | 5 | 5 | 60 |
| 31 | 10 | 10 | 10 | 5 | 5 | 60 |
| 9 | 10 | 10 | 5 | 2.5 | 5 | 40 |
| 10 | 10 | 10 | 5 | 5 | 10 | 60 |
| 11 | 10 | 10 | 10 | 5 | 5 | 40 |
| 13 | 10 | 10 | 5 | 5 | 5 | 40 |
| 14 | 10 | 10 | 10 | 5 | 10 | 60 |
| 17 | 10 | 10 | 10 | 5 | 2.5 | 40 |
| 18 | 10 | 10 | 10 | 5 | 5 | 40 |
| 15 | 20 | 20 | 10 | 10 | 10 | 60 |
| 36 | 10 | 10 | 5 | 5 | 5 | 40 |
| 32 | 10 | 5 | 5 | 2.5 | 2.5 | 40 |

EXAMPLE 25

The emulsifiable concentrates which were prepared by Example 20 were diluted with water 400 times and 800 times to form emulsions.

The square plates of beach of which a side was 5 cm long and thickness was 5 mm were dipped into the emulsion for 2 minutes and dried for 24 hours at room temperature.

The square plates were placed on the surface of agar plates. The suspensions which contained spores of *Aspergillus niger*, *Penicillium citrinum*, *Cladosporium harbarum* and *chaetomium globosum* were respectively sprayed on the agar plates and the square plates.

The test fungi were cultivated in the incubator at the humidity of 95% and the temperature of 28° C for 2 weeks. The results are shown in Table 11. The degree of growth inhibition is defined in terms of the following numerical ratings.

Table 11

| Compound No. | Degree of growth inhibition Concentrate of active compound | |
|---|---|---|
| | 0.025 % | 0.0125 % |
| 2 | 3 | 2 |
| 6 | 3 | 3 |
| 7 | 5 | 5 |
| 25 | 3 | 2 |
| 29 | 3 | 2 |
| 8 | 3 | 3 |
| 9 | 3 | 3 |
| 10 | 3 | 3 |
| 13 | 3 | 2 |
| 17 | 3 | 2 |
| 18 | 3 | 2 |
| No treatment | 1 | 1 |

EXAMPLE 26

The emulsifiable concentrates which were prepared by Example 20 were diluted with water 100 times to form an emulsion.

A cloth of cotton was soaked into each emulsion for 2 minutes. The clothes were dried at room temperature and cut into a square of which a side was 1 cm long. Each kind of test bacteria and fungi was inoculated, separately, on plates of potato-agar and one square cloth placed on each of such plates. Test bacteria and fungi were cultivated at 28° C for 4 days. The width of the region of growth-inhibition which was formed a circumference of the cloth was measured. The results are shown in Table 12.

Table 12

| Compound No. | The width of the region of growth-inhibition(mm) | | | |
|---|---|---|---|---|
| | Fungi | | Bacteria | |
| | Aspergillus niger | Penicillium citrinum | Bacillus subtilis | Staphylococcus oureus |
| 2 | 5 | 5 | 9 | 10 |
| 6 | 5 | 7 | 9 | 7 |
| 7 | 10 | 10 | 12 | 11 |
| 25 | 6 | 5 | 6 | 6 |
| 9 | 6 | 6 | 9 | 7 |
| 13 | 6 | 7 | 7 | 6 |
| 17 | 5 | 6 | 8 | 7 |
| No treated | 0 | 0 | 0 | 0 |

EXAMPLE 27

Zero point zero two (0.02) part of active compounds in the form of 10% water soluble concentrate which was prepared by Example 23 was added into 100 parts of Waxman's liquid medium. Peices of Wood iron (hereafter referred to as the slime test boards) were soaked into the Waxman's liquid medium. The bacteria which were gathered from circular water system were inoculated upon the Waxman's liquid medium and incubated at 27°-34° C by shaking culture for 2 days. The degree of propagation of the bacteria on the slime test boards was examined.

The growth-inhibiting activity of active compounds against the fungi and the green algae was also examined by the same method as mentioned above.

The results are shown in Table 13.

The degree of propagation of the bacteria, fungi or green algae on the test boards is defined in terms of the following symbols.

Table 13

| Compound No. | Degree of propagation | | |
|---|---|---|---|
| | Bacteria | Fungi | Green Algae |
| 2 | − | − | − |
| 6 | − | − | − |
| 7 | − | − | − |
| 21 | − | − | − |
| 25 | + | + | + |
| 9 | − | − | − |
| 10 | + | − | − |
| 13 | − | − | − |
| 17 | − | + | + |
| No treatment | + + + + | + + + + | + + + + |

− : propagation
+ : the area of propagation is 1–25% on the slime test boards.
+ + : the area of propagation is 26–50% on the slime test boards.
+ + + : the area of pro agation is 51–75% on the slime test boards.
+ + + + : the area of propagation is 76–100% on the slime test boards.

We claim:

1. The method for killing bacteria, fungi and algae comprising applying to materials vulnerable thereto an effective amount of one or more compounds of the formula

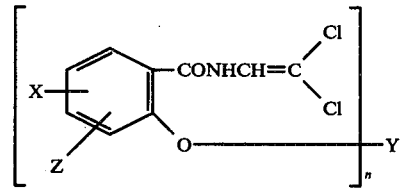

where X represents hydrogen atom, chlorine atom, bromine atom, methyl group or nitro group, Y represents hydrogen atom, methyl group, an alkylcarbonyl group where the alkyl group has from 1 to 12 carbon atoms, and may be substituted by one or more halogen atoms, a lower alkoxy carbonyl group, a lower alkylamino carbonyl group or a metal atom of which the valence is 1 or 2, Z represents hydrogen atom or chlorine atom and n represents 2 when Y represents a divalent metal and n represents 1 when Y does not represent a divalent metal.

2. A method according to claim 1 wherein, in said formula, said alkyl group in said alkyl carbonyl group has from 1 to 3 carbon atoms, the lower alkoxy in said lower alkoxy carbonyl group has from 1 to 4 carbon atoms, said lower alkylamino carbonyl group is a methylamino carbonyl group, and said metal atom is selected from the group consisting of sodium, potassium, zinc and manganese.

3. A method according to claim 1 wherein said materials comprise industrial raw materials, industrial products or water in circular water systems.

4. A method according to claim 1 wherein said materials comprise plants, seeds of plants, or soil intended for or used by plants.

5. A method for killing bacteria, fungi and algae according to claim 3 comprising applying to industrial raw materials, industrial products or water in circulating water systems an effective amount of one or more compounds of N-($\beta$, $\beta$-dichlorovinyl) salicylamide or a metallic salt thereof.

6. The method for killing bacteria, fungi and algae according to claim 5 wherein the materials treated are organic industrial raw materials or products.

7. The method for killing bacteria, fungi and algae according to claim 5 wherein the compounds are N-($\beta$, $\beta$-dichlorovinyl) salicylamide or metallic salts thereof where the valence of the metallic atom is one or two.

8. The method for killing bacteria, fungi and algae according to claim 5 wherein the compound is one of the compounds selected from the group consisting of N-($\beta$, $\beta$-dichlorovinyl) salicylamide, sodium salt of N-($\beta$, $\beta$-dichlorovinyl) salicylamide, potassium salt of N-($\beta$, $\beta$-dichlorovinyl) salicylamide and zinc salt of N-($\beta$, $\beta$-dichlorovinyl) salicylamide.

* * * * *